(12) United States Patent
Lockhart et al.

(10) Patent No.: US 10,632,263 B2
(45) Date of Patent: Apr. 28, 2020

(54) APPARATUS AND METHOD FOR IMPROVED MEDICATION DOSING

(71) Applicant: Becton, Dickinson and Company, Franklin Lakes, NJ (US)

(72) Inventors: Artis Lockhart, Durham, NC (US); Lawrence Monahan, Fuquay Varina, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 641 days.

(21) Appl. No.: 14/649,890

(22) PCT Filed: Dec. 6, 2012

(86) PCT No.: PCT/US2012/068225
§ 371 (c)(1),
(2) Date: Jun. 4, 2015

(87) PCT Pub. No.: WO2014/088582
PCT Pub. Date: Jun. 12, 2014

(65) Prior Publication Data
US 2015/0306318 A1    Oct. 29, 2015

(51) Int. Cl.
*A61M 5/315* (2006.01)
*A61M 5/31* (2006.01)

(52) U.S. Cl.
CPC .......... *A61M 5/31511* (2013.01); *A61M 5/31* (2013.01); *A61M 5/31593* (2013.01); *A61M 2005/3125* (2013.01); *A61M 2005/3126* (2013.01); *A61M 2205/583* (2013.01); *A61M 2205/584* (2013.01); *A61M 2205/585* (2013.01); *A61M 2205/587* (2013.01)

(58) Field of Classification Search
CPC ...... A61M 2205/583; A61M 2205/585; A61M 2005/3125; A61M 2005/3126; A61M 5/31; A61M 5/31511; A61M 5/31593
See application file for complete search history.

(56) References Cited

U.S. PATENT DOCUMENTS

| | | | | |
|---|---|---|---|---|
| 2,902,034 A | * | 9/1959 | Simmonds ........ | A61M 5/31513 604/222 |
| 3,596,659 A | * | 8/1971 | Glasser ............... | A61M 5/1785 604/187 |
| 4,743,234 A | * | 5/1988 | Leopoldi ............. | A61M 5/3129 604/187 |

(Continued)

FOREIGN PATENT DOCUMENTS

| | | |
|---|---|---|
| CN | 201798974 U | 4/2011 |
| WO | WO-2007014428 A1 | 2/2007 |

*Primary Examiner* — Nathan R Price
*Assistant Examiner* — Anh Bui
(74) *Attorney, Agent, or Firm* — Dickinson Wright PLLC

(57) ABSTRACT

An apparatus and method for improving medication dosing is provided. The apparatus preferably includes a template configured to fit over a barrel of a syringe, the template having a substantially opaque exterior and at least one substantially transparent section in the substantially opaque exterior permitting a view of the syringe barrel and a distal end of a plunger within the barrel of the syringe. A method includes the steps of positioning a dosing template on a syringe, operating a plunger within the syringe, and drawing a predetermined dose of medication into the syringe.

29 Claims, 2 Drawing Sheets

(56) References Cited

U.S. PATENT DOCUMENTS

| | | | | |
|---|---|---|---|---|
| 5,498,243 A | * | 3/1996 | Vallelunga | A61M 5/3243 604/187 |
| 6,120,481 A | * | 9/2000 | Rennert | A61M 5/3129 604/186 |
| 9,155,839 B1 | * | 10/2015 | Willis | A61M 5/31 |
| 2002/0088131 A1 | * | 7/2002 | Baxa | A61M 5/31525 33/494 |
| 2010/0164137 A1 | * | 7/2010 | Selkee | A61M 25/0136 264/242 |
| 2012/0089098 A1 | * | 4/2012 | Boyd | A61M 5/24 604/189 |

* cited by examiner

APPARATUS AND METHOD FOR IMPROVED MEDICATION DOSING

FIELD OF THE INVENTION

The present invention generally relates to an apparatus and method for improved medication dosing. In particular, the present invention is directed to a syringe template that may be used by an individual requiring a regular dose of a substance, such as insulin, to be injected intravenously. The template may be used to modify a syringe to better measure and dispense any number of substances to be administered, such as by an injection.

BACKGROUND OF THE INVENTION

Those who suffer from diabetes must control the level of blood sugar in their bloodstream on a daily, and sometimes hourly, basis. Insulin is only effective when injected directly into the bloodstream where it may be used by the body to counter/neutralize the effects of excessive blood sugar accumulation. Those who suffer from diabetes and their caregivers must become adept at determining the diabetic's blood sugar, calculating the correct dosage of insulin required to help return the blood sugar level to a normal range, loading a syringe with the calculated dosage, and administering the calculated dose through the use of the loaded syringe.

A standard syringe, as commonly available, consists of a hollow needle attached to the body of the syringe, also called the syringe barrel. The syringe barrel is a cylinder, into which a plunger is inserted, and that has a diameter calibrated such that a particular length of the barrel corresponds to a measured volume. The calibration volume is indicated by markings on the exterior surface of the syringe barrel. The user loads a syringe by placing the plunger at full depth in the syringe barrel such that the inserted end of the plunger is in contact with the base of the syringe barrel where the needle is attached to the barrel. The hollow needle is inserted into the compound, typically in liquid form, and the plunger is then pulled away from the end of the syringe barrel. When the plunger is pulled outward a gasket surrounding the plunger that is in contact with the interior wall of the syringe barrel is sufficient to cause a partial vacuum of sufficient strength to draw the compound into the syringe barrel via the hollow needle. The user watches the markings on the side of the barrel until the desired amount of the compound is drawn into the syringe. The user may then insert the hollow needle into an appropriate place on the body of the user, or another whom the user is assisting, and reverse the motion of the plunger to eject the compound from the syringe barrel into the body of the person who requires the compound. In the case of a diabetic the compound may be insulin.

A concern in the use of a standard syringe is that markings on the syringe barrel may be difficult to discern for a person who has diminished eyesight, for example, due to the detrimental effects to eyesight some diabetics experience. An additional concern is that the user may be unfamiliar with the dosage calculations, or may be uncertain as to how to know when the required dosage has been drawn into the syringe barrel and, as a result, draw too much or too little of the compound into the syringe barrel. A final concern is that the user, whether it is the diabetic or a caregiver, may be distracted and draw an inaccurate amount of the compound into the syringe barrel through simple inattention.

BRIEF DESCRIPTION OF THE INVENTION

The invention is drawn toward addressing the concerns of discovering and correcting inaccurate dosages drawn into the syringe barrel prior to injecting the compound into a patient. In an exemplary embodiment, the compound that is being drawn into the body of the syringe is insulin and the patient who is to receive the injection is a diabetic who requires the insulin to control the level of sugar in the bloodstream. Injecting the wrong amount of insulin can have very serious effects upon a diabetic. For this reason, modifying a standard syringe to permit a user or caregiver to more easily see the level of insulin in the body of the syringe and simplify reading the dosage on the standard syringe will provide a more accurate dosage and a more user friendly interaction with the syringe. It is understood, however, that the device of the present invention could be used with a variety of injectable compounds and is not limited to insulin.

In one embodiment, a device for improving medication dosing is provided. The device may include a template configured to fit over a barrel of a syringe, the template having an substantially opaque exterior and at least one substantially transparent window in the substantially opaque exterior permitting a view of the syringe barrel and a distal end of a plunger within the barrel of the syringe. The distal end of the plunger inserted within the barrel of the syringe may include a different color than the rest of the plunger. The color of the distal end of the plunger may be a high visibility/contrast color. The distal end of the plunger may be configured to glow in the dark. The template may be removably attached to the barrel of the syringe. The template may interlock with a flange of the barrel of the syringe to hold the template in an appropriate position with respect to the barrel of the syringe. The template length may be modified to indicate a calibrated dosage according to the length of the template when the template is attached to the barrel of the syringe. The at least one substantially transparent window in the opaque exterior may be positioned to indicate a particular volume of medication when the distal end of the plunger is correctly positioned within the at least one substantially transparent window. The at least one substantially transparent window may include a plurality of substantially transparent windows, each indicating a particular volume of medication when the distal end of the plunger is positioned within a particular one of the substantially transparent windows. The plurality of substantially transparent windows may be color coded to indicate particular dosages. The at least one substantially transparent window may include a magnifying window.

In another embodiment, an apparatus for improving medication dosing is provided. The apparatus may include a template configured to fit over a barrel of a syringe, the syringe may have an internal plunger with a plunger stopper at a distal end of the internal plunger configured to fit within the barrel of the syringe, the template may have a substantially opaque exterior and at least one substantially transparent window in the substantially opaque exterior permitting a view of the syringe barrel and plunger stopper within the barrel of the syringe where the at least one substantially transparent window in the substantially opaque exterior may be positioned to indicate a particular volume of medication when the plunger stopper of the plunger is correctly positioned within the at least one substantially transparent window.

In yet another embodiment, a device for improving medication dosing is provided. The device may include a syringe having a plunger insertable within a barrel of the syringe; and a template configured to fit over the barrel of the syringe, the template having a substantially opaque exterior and at least one substantially transparent window in the substantially opaque exterior permitting a view of the barrel of the syringe and plunger within the syringe barrel. The stopper may include a plunger stopper at a distal end of the plunger.

In still yet another embodiment, a method of determining a medication dose is provided. The method may include positioning a dosing template having at least one substantially transparent window formed in the template over a barrel of a syringe; placing a plunger within the barrel of the syringe until a distal end of the plunger is in contact with an internal bottom end of the barrel; pulling the plunger such that the distal end of the plunger is pulled away from contact with the internal bottom end of the barrel of the syringe; and drawing a medication into the barrel of the syringe until the distal end of the plunger is correctly positioned within the substantially transparent window of the template where the transparent window is calibrated to draw a predetermined dose of a medication when the distal end of the plunger becomes visible in the substantially transparent window of the template.

BRIEF DESCRIPTION OF THE DRAWINGS

Various inventive embodiments disclosed herein, both as to its organization and manner of operation, together with further objectives and advantages, may be best understood by reference to the following description, taken in connection with the accompanying drawings as set forth below.

DETAILED DESCRIPTION OF THE INVENTION

The present invention discloses a modification to a standard syringe to address the concerns for over or under-filling the syringe barrel, delivering an accurate dose of medication, and correcting for any inattention or distraction of a caregiver in the use of the modified syringe. The syringe becomes an easy to use device by adding a specially designed template to the outside of the barrel and may include color-coding the outer exposed portion of a plunger stopper. The plunger rod is pulled back until the plunger stopper is exposed in the template window, which makes the medication dosage accurate and reproducible.

Figure 1:
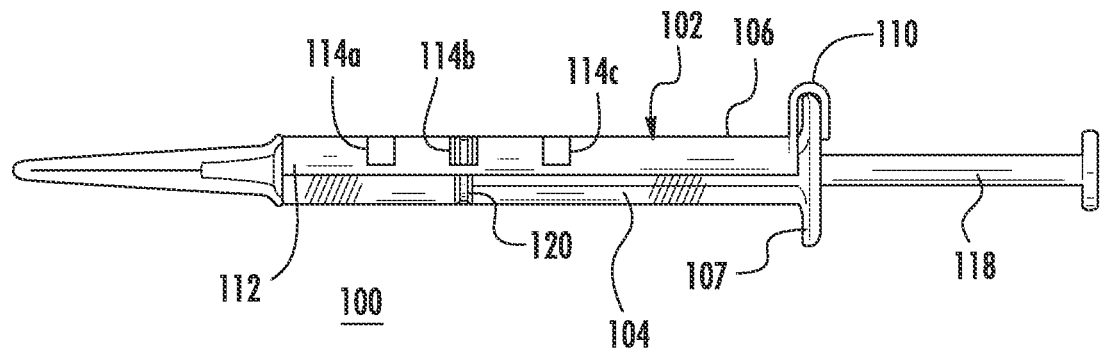
FIG. 1 illustrates a standard syringe with an attached template consistent with certain embodiments of the invention.

FIG. 1 presents an exemplary view of a typical syringe 100 with an attached template 102 consistent with certain embodiments of the invention. The template 102 preferably is of a partial hollow cylinder shape with an internal diameter sufficient to permit attachment of the template 102 to a syringe barrel 104 of syringe 100, such that the syringe barrel 104 is substantially enclosed by the template 102. The template 102 is preferably of a sufficient diameter to fit snugly over the syringe barrel 104. While it is understood that template 102 may be affixed to syringe 100 through a variety of methods (including adhesive as discussed with reference to FIG. 2 below), template 102 preferably attaches to the syringe barrel 104 through a press fit, where the template 102 is some degree smaller in diameter than the syringe barrel 104 in its normal state and upon pressing the template 102 onto the syringe barrel 104, the template 102 widens slightly as it passes over the syringe barrel 104 and then narrows slightly as it is "pressed" in place, securing the template 102 to the syringe barrel 104. In some embodiments, a proximal end 106 of the template 102 can be in contact with a flange 107 of the syringe barrel 104. In a preferred embodiment, proximal end 106 of template 102 is configured to include a channel 110 to interlock with flange 107 to secure the template 102 in position when attached to syringe barrel 104 (thereby keeping template 102 from shifting along the length of syringe barrel 104).

In one embodiment, the template 102 when installed on the syringe barrel 104 does not cover the entirety of the syringe barrel 104 circumference. In this embodiment, the template 102 has a diameter that is sufficient to maintain the template 102 in place once installed on the syringe barrel 104, but provides an opening through which the graduated markings on the syringe barrel 104 remain visible.

Template 102 preferably has a substantially opaque outer coating 112 that has one or more transparent windows 114 (shown as windows 114a, 114b, and 114c) in the coating to permit a user to see the syringe barrel 104, the markings on the syringe barrel 104, and a plunger stopper 120 at an end of a plunger 118 of syringe 100 when the plunger 118 is at the correct position to be aligned with the one or more template windows 114. By being described as transparent, it is understood that the window(s) 114 can be made of transparent (i.e., substantially see-through) material, can be cut-out holes in opaque coating 112, or can be other configurations such that plunger stopper 120 is viewable through window 114.

Positioning the plunger 118 within the syringe barrel 104 such that the plunger stopper 120 end of the plunger 118 is visible within a template window 114 indicates a calibrated dosage of medication is in the syringe barrel 104 of the syringe 100. A key advantage of using the template 102 over using a syringe 100 without the template 102 is that the template 102 simplifies determining the dosage of the medication loaded in the syringe barrel 104. The template 102 can be designed for single or multiple dosage readings. In one embodiment, as a reusable device, the template 102 may be used on a first syringe 100, removed from that syringe 100 as the syringe 100 is discarded and placed on a second syringe 100 in preparation for a new dose measurement. The template windows 114 simplify the ability to determine when a calibrated dose has been measured into the syringe barrel 104 and provide a more user friendly experience thereby.

In an alternative embodiment, the template 102 may have a plurality of windows 114a, 114b, and 114c. In this exemplary embodiment, each window 114 could be positioned such that the position is calibrated for a different dosage level of medication, such as insulin, which may be needed at different times of the day (e.g., breakfast, lunch, and dinner). Filling the syringe 100 to differing levels of each separate window 114 would present a different dosage within the syringe barrel 104 for each window 114 in the template 102. Further still, the windows 114 may be color coded, such as by tinting or outlining, to help distinguish differing dosage measurements.

Figure 2:
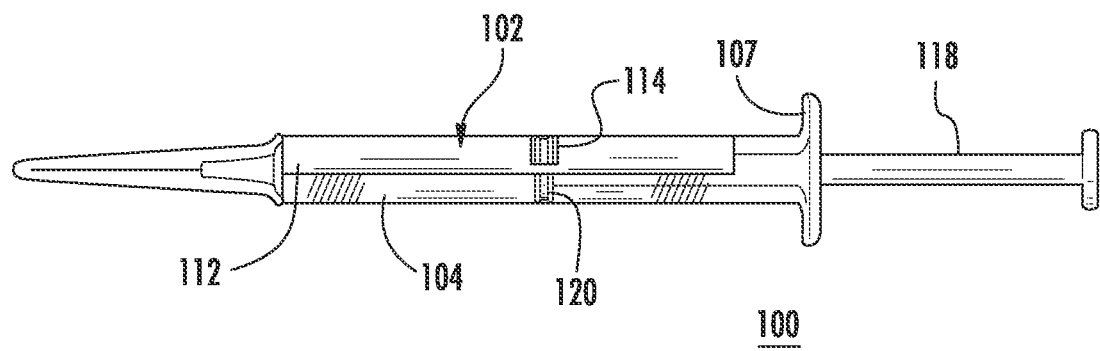
FIG. 2 illustrates a view of a color-coded plunger stopper viewed within a template window consistent with certain embodiments of the invention.

FIG. 2 presents a view of the plunger stopper 120 viewed within a template window 114 consistent with certain embodiments of the invention. In an exemplary embodiment, the plunger stopper 120 may be color-coded, such as with a high contrast/visibility color or colors, to permit enhanced visibility of the plunger stopper 120 within window 114 excised in the opaque coating 112 of the template 102. The simplified design of the template 102, in combination with the plunger stopper 120, which may be color coded, makes determining an accurate dosage much easier for a user, but it is especially useful for the visually impaired. Determining an accurate dosage is simplified by using the plunger stopper 120, which may be color coded, to indicate to a user or caregiver when the end of the plunger stopper 120 is correctly positioned within the dosage window 114 of the template 102. Creating the plunger stopper 120 with color coding, is easily accomplished in the manufacturing process through the application of coloring(s) to the plunger stopper 120, or by wrapping the plunger stopper 120 with an appropriate color-coded material that adheres to the plunger stopper 120, making the plunger stopper 120, with color coding, cost effective to produce.

The plunger stopper 120 may be modified to change colors, for example, the plunger stopper 120 may be designed to glow in the dark. This greater visibility in low light conditions and multiple dosage calibration permits greater accuracy in filling the syringe 100 under various lighting and ambient conditions. In one embodiment, window 114 of template 102 may include a magnifying window. By adding a magnifying window to the template 102, the plunger stopper 120 would be more readily visible to those who have vision issues and provide greater utility for those who require such assistance.

The template 102 shown in FIG. 2 is shown without channel 110 that attaches to flange 107 and template 102 as shown doesn't reach all the way along the length of syringe barrel 104. The template 102 of such an arrangement may be secured to syringe barrel 104 through adhesives, press fit, or any other method of attachment. The form of attachment (i.e., fixed or removable) determines whether the template is reusable as discussed above. It is understood that the various options (i.e., number of windows 114, coloring of plunger stopper 120, length of template 102, magnifying windows, fit method, etc.) as discussed herein can be interchangeable in accordance with the invention discussion herein.

In an additional alternative embodiment, the template 102 may be comprised of a number of removable sections. In this non-limiting embodiment, the template 102 may have sections calibrated such that the length of a particular section, when attached to the syringe barrel 104 of the syringe 100, would represent a particular dosage of medication. The sections of the template may be perforated to permit a user to remove those sections of the template 102 that did not indicate the desired dosage leaving only the section(s) required to indicate the required calibrated dosage. The template 102, thus calibrated, would then be attached to the syringe barrel 104 of the syringe 100 to assist the user or caregiver in filling the syringe 100 with the required dosage. In use the user may remove the appropriate removable section of template 102, for example by snapping or tearing it at the appropriate perforation, and attaching it to the syringe barrel 104. The user would preferably then load the syringe with medication, using conventional techniques, loading the syringe up to the top of the attached template 102 section, the top of the attached template 102 section in effect being the window as described herein.

Figure 3:
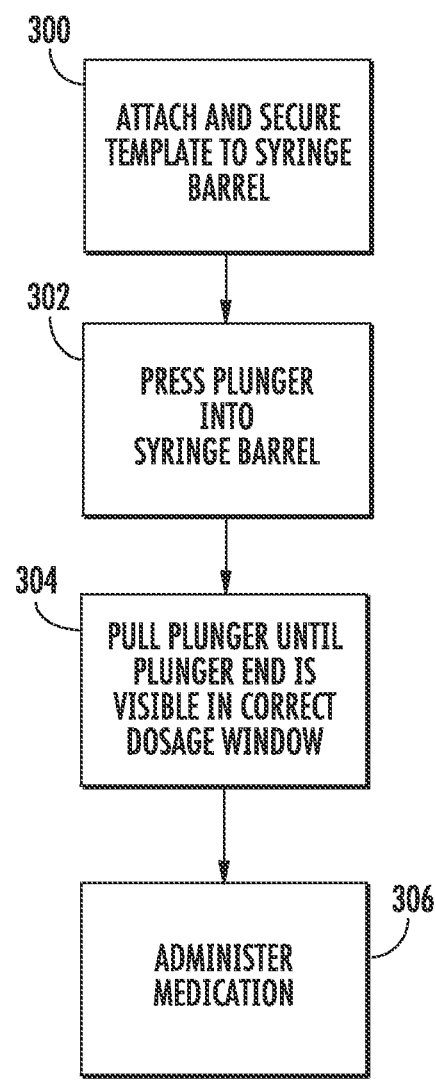
FIG. 3 illustrates a method for use of a syringe and template consistent with certain embodiments of the invention.

FIG. 3 illustrates a flow diagram of an example of a method for use of the syringe template 102 with a syringe 100 consistent with certain embodiments of the invention. In this exemplary embodiment, a user or a caregiver is using a syringe 100 and has a template 102 having one or more dosage windows 114 within or incised through the substantially opaque coating 112 of the template 102.

At a step 300, the user or caregiver attaches the template 102 to the syringe barrel 104 of the syringe 100 by positioning template 102 on the syringe barrel 104 such that the proximal end 106 of template 102 preferably interlocks with flange 107 (in one embodiment), and applying pressure to permit a secure fit of the template 102 onto the syringe barrel 104 and locking it into place.

At a step 302, the user or caregiver may then depress the plunger 118 into the syringe barrel 104 of the syringe 100 in preparation for drawing a measured dose of medication, such as insulin, into the syringe barrel 104 of the syringe 100.

At a step 304, the user or caregiver pulls the plunger 118 back until the plunger stopper 120, which may be colored with a high visibility/contrast coloring, is correctly positioned in the desired dosage window 114. When the user or caregiver can discern the plunger stopper 120 is correctly positioned in the dosage window 114, the proper dose of medication has been drawn into the syringe barrel 104 of the syringe 100.

At a step 306, the measured dose of medication may then be administered to the user.

The described invention is sufficient to provide a user or caregiver with a more visible and accurate dosage of insulin or other medication in the syringe barrel 104 of the syringe 100. The medication may be administered to the user and, in one embodiment, the syringe template 102 can be removed from the syringe 100 and re-used on another, separate syringe 100. The template 102 and plunger stopper 120, preferably with color coding or other visual enhancement indicator, provide a more accurate and user-friendly capability to measure and administer medications, such as insulin.

CONCLUDING REMARKS

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. It will be understood that various details of the present invention may be changed without departing from the scope of the present invention. Furthermore, the foregoing description is for the purpose of illustration only, and not for the purpose of limitation.

We claim:

1. An apparatus for improving medication dosing comprising:
   a syringe having a barrel for containing a medication, a plunger movable within the barrel to draw in and dispense the medication, and a flange on the barrel; and
   a reusable template configured to fit over the barrel and to be removable from the barrel after use of the syringe, the template having a length aligned with a longitudinal axis of the barrel and a substantially opaque exterior, the template defining at least one substantially transparent window formed by a cut-away portion of the substantially opaque exterior and permitting a view of the barrel and a distal end of the plunger within the barrel, the at least one substantially transparent window not being coextensive with the length of the template and being positioned to indicate a particular dosage of medication only when the distal end of the plunger is correctly positioned with respect to the at least one substantially transparent window.

2. The device of claim 1, where the distal end of the plunger comprises a different color than the rest of the plunger.

3. The device of claim 2, where the color of the distal end of the plunger is a high visibility/contrast color.

4. The device of claim 2, where the distal end of the plunger is configured to glow in the dark.

5. The device of claim 1, where the template interlocks with the flange to hold the template in an appropriate position with respect to the barrel.

6. The device of claim 1, where the template length is modified to indicate a calibrated dosage according to the length of the template when the template is attached to the barrel.

7. The device of claim 1, where the at least one substantially transparent window comprises a plurality of substantially transparent windows, each indicating a particular dosage of medication when the distal end of the plunger is correctly positioned with respect to a particular one of the substantially transparent windows.

8. The device of claim 7, where the plurality of substantially transparent windows are color coded to indicate particular dosages.

9. The device of claim 1, where the at least one substantially transparent window comprises a magnifying window.

10. An apparatus for improving medication dosing comprising:
a syringe having a barrel for containing a medication, an internal plunger with a plunger stopper at a distal end of the internal plunger configured to fit within the barrel to draw in and dispense the medication, and a flange on the barrel; and
a reusable template configured to fit over the barrel and to be removed from the barrel after use of the syringe, the template having a length aligned with a longitudinal axis of the barrel and a substantially opaque exterior, the template defining at least one substantially transparent window formed by a cut-away portion of the substantially opaque exterior and permitting a view of the barrel and plunger stopper within the barrel, where the at least one substantially transparent window is not coextensive with the length of the template and is positioned to indicate a particular volume of medication only when the plunger stopper is correctly positioned with respect to the at least one substantially transparent window.

11. The apparatus of claim 10, where the plunger stopper is a different color than the rest of the plunger.

12. The apparatus of claim 11, where the color of the plunger stopper is a high visibility/contrast color.

13. The apparatus of claim 11, where the plunger stopper is configured to glow in the dark.

14. The apparatus of claim 10, where the at least one substantially transparent window comprises a plurality of substantially transparent windows, each indicating a particular volume of medication when the distal end of the plunger is positioned with respect to a particular one of the substantially transparent windows.

15. The apparatus of claim 14, where the plurality of substantially transparent windows are color coded to indicate particular dosages.

16. The apparatus of claim 10, where the at least one substantially transparent window comprises a magnifying window.

17. An apparatus for improving medication dosing comprising:
a syringe having a barrel for containing a medication, a plunger insertable within the barrel to draw in and dispense the medication, and a flange on the barrel; and
a reusable template configured to fit over the barrel and to be removed from the barrel after use of the syringe, the template having a length aligned with a longitudinal axis of the barrel and a substantially opaque exterior, the template defining at least one substantially transparent window formed by a cut-away portion of the substantially opaque exterior and permitting a view of the barrel and plunger within the barrel, where the at least one substantially transparent window is not coextensive with the length of the template and is positioned to indicate a particular volume of medication only when the plunger is correctly positioned with respect to the at least one substantially transparent window.

18. The apparatus of claim 17, further comprising a plunger stopper at a distal end of the plunger.

19. The apparatus of claim 18, where the plunger stopper is a different color than the rest of the plunger.

20. The apparatus of claim 18, where the color of the plunger stopper is a high visibility/contrast color.

21. The apparatus of claim 18, where the plunger stopper is configured to glow in the dark.

22. The apparatus of claim 17, where the template has a plurality of substantially transparent windows, each window indicating a particular volume of medication when the plunger is correctly positioned with respect to a particular one of the substantially transparent windows.

23. A method of administering a medication dose, comprising:
providing a syringe having a barrel for containing a medication, a plunger movable within the barrel to draw in and dispense the medication, and a flange on the barrel;
positioning a reusable dosing template over the barrel, the template having a length aligned with a longitudinal axis of the barrel and a substantially opaque exterior, the template defining at least one substantially transparent window formed by a cut-away portion of the substantially opaque exterior and permitting a view of the barrel and plunger within the barrel, the at least one substantially transparent window not being coextensive with the length of the template;
placing a plunger within the barrel until a distal end of the plunger is in contact with an internal bottom end of the barrel;
pulling the plunger such that the distal end of the plunger is pulled away from contact with the internal bottom end of the barrel;
drawing a medication into the barrel until the distal end of the plunger is correctly positioned with respect to the substantially transparent window of the template, where the substantially transparent window is calibrated to draw a predetermined dose of a medication when the distal end of the plunger is so positioned;
pushing the plunger to dispense the predetermined dose of medication from the syringe; and
removing the template from the syringe.

24. The method of claim 23, where the at least one substantially transparent window comprises a magnifying window.

25. The method of claim 23, where the at least one substantially transparent window comprises a plurality of substantially transparent windows, each indicating a particular volume of medication when the distal end of the plunger is positioned with respect to a particular one of the substantially transparent windows.

26. The apparatus of claim 25, where the plurality of substantially transparent windows are color coded to indicate particular dosages.

27. The method of claim 23, where the distal end of the plunger comprises a high visibility/contrast color.

28. The method of claim 23, where the distal end of the plunger is configured to glow in the dark.

29. The method of claim 23, further comprising:
reusing the template with another syringe.

* * * * *